United States Patent [19]
Buechler et al.

[11] Patent Number: 6,106,779
[45] Date of Patent: Aug. 22, 2000

[54] LYSIS CHAMBER FOR USE IN AN ASSAY DEVICE

[75] Inventors: Kenneth F. Buechler, San Diego; Jason Christopher Briggs, Carlsbad; Scott Harold Rongey, San Diego, all of Calif.

[73] Assignee: Biosite Diagnostics, Inc., San Diego, Calif.

[21] Appl. No.: 08/942,370

[22] Filed: Oct. 2, 1997

[51] Int. Cl.[7] .............................. G01N 21/00; G01N 1/30; C12M 1/00; H01L 21/14

[52] U.S. Cl. ......................... 422/55; 422/53; 422/57; 422/58; 422/61; 422/62; 422/73; 422/102; 422/122; 422/145; 422/68.1; 436/169; 436/170; 436/52; 436/63; 436/164; 436/522; 436/524; 436/809; 435/287.1; 435/287.2; 435/289.1; 435/288.7; 424/3

[58] Field of Search ..................... 422/56, 57, 55, 422/58, 61, 62, 73, 102, 68.1, 122, 145; 436/169, 170, 63, 52, 522, 164, 809, 524; 435/287.2, 289.1, 288.7, 287.1, 34, 39; 424/3

[56] References Cited

U.S. PATENT DOCUMENTS

| | | | |
|---|---|---|---|
| 4,751,179 | 6/1988 | Ledis et al. | 435/34 |
| 4,906,439 | 3/1990 | Grenner et al. | 422/56 |
| 5,304,487 | 4/1994 | Wilding et al. | 435/291 |
| 5,458,852 | 10/1995 | Buechler | 422/58 |
| 5,460,777 | 10/1995 | Kitajima et al. | 422/56 |
| 5,486,335 | 1/1996 | Wilding et al. | 422/55 |
| 5,498,392 | 3/1996 | Wilding et al. | 422/68 |
| 5,558,834 | 9/1996 | Chu et al. | 422/55 |
| 5,587,128 | 12/1996 | Wilding et al. | 422/50 |
| 5,635,358 | 6/1997 | Wilding et al. | 435/7.2 |
| 5,726,026 | 3/1998 | Wilding et al. | 435/7.21 |
| 6,007,690 | 12/1999 | Nelson | 204/601 |

FOREIGN PATENT DOCUMENTS

| | | |
|---|---|---|
| 0 447 154 A2 | 9/1991 | European Pat. Off. |
| 93/24231 A1 | 12/1993 | WIPO |
| 95/07468 | 3/1995 | WIPO |

OTHER PUBLICATIONS

Woolley et al. Ultra–HighSpeed DNA fragment separations using microfabricated capillary array electrophoresis chips. Proc. Natl. Acad. Sci. USA vol. 91, Nov. 1994, pp. 11348–11352.

Effenhauser et al. High–Speed Separation of Antisense Oligonucleotides on a Micromachined Capillary Electrophoresis Device. Analytical Chemistry vol. 66, No. 18, Sep. 15, 1994, pp. 2949–2953.

*Primary Examiner*—Christopher L. Chin
*Assistant Examiner*—Pensee T. Do
*Attorney, Agent, or Firm*—Brobeck, Phleger & Harrison LLP

[57] ABSTRACT

A lysis chamber of an assay device capable of producing lysis of cells in a sample fluid such as whole blood, said chamber comprising a surface which contacts the sample fluid when the sample fluid is placed into the assay device; and a lytic material immobilized on the surface, whereby cells of the sample fluid are lysed when they contact the lytic material. The chamber can delimit a capillary space, and lytic material can be saponin or a detergent. Methods employing devices comprising such chambers can assay for whole blood amounts of cyclosporin or hemoglobin A1c.

14 Claims, 3 Drawing Sheets

*Mesh Located in Lysis Chamber*

*Direction of Sample Flow*

LYSIS CHAMBER FOR USE IN AN ASSAY DEVICE

FIELD OF THE INVENTION

This invention relates to assay devices. More particularly, the lysis chamber is a chamber of capillary space dimension comprising a lytic component on a surface thereof.

BACKGROUND ART

With the advent of point of care testing in medical settings, it has become increasingly important to have diagnostic products which are simple, rapid and convenient for the user to perform. Thus, health care workers in emergency settings need results rapidly, and have minimal time to perform a diagnostic test. The rapid availability of a diagnostic result allows a physician to treat a patient as soon as possible.

Point of care diagnostic tests often are performed on biological samples, such as whole blood or urine. However, cells and particulate matter in biological samples can interfere with fluid flow in a test device, and thus impair the measurement of analytes in the biological fluid.

For example, in blood samples, red blood cells can interfere with spectroscopic measurements; such interference is further affected by hematocrit, since as the hematocrit varies, the volume of plasma in a given volume of blood varies. To overcome these problems, red blood cells are often separated from plasma to allow for a more defined and uniform sample.

For certain analytes to be assayed in a blood sample, however, analysis of plasma or serum does not accurately reflect the amount of the analyte in the biological sample. For example, therapeutic agents such as cyclosporin, or metabolic molecules such as hemoglobin and hemoglobin A1c (HbA1c), need to be evaluated in both extracellular and intracellular spaces to obtain an effective assay result. To evaluate analyte levels both intracellularly and extracellularly, cellular components are lysed, and thereafter a liquid sample containing mixed extracellular and intracellular fluids is assayed.

Assay results for analytes such as hemoglobin, hemoglobin A1c and cyclosporin are often needed on a point of care basis. Accordingly, there is a need for assay devices that permit rapid assay results of an analyte present in extracellular and intracellular compartments of a biological sample.

Thus, there is a need for an efficient, compact, cost-effective device structure to facilitate lysis of cells in biological samples. There is also a need for devices that achieve cellular lysis and thereafter provide an assay result on both extracellular and intracellular contents.

DISCLOSURE OF THE INVENTION

Figure 1:
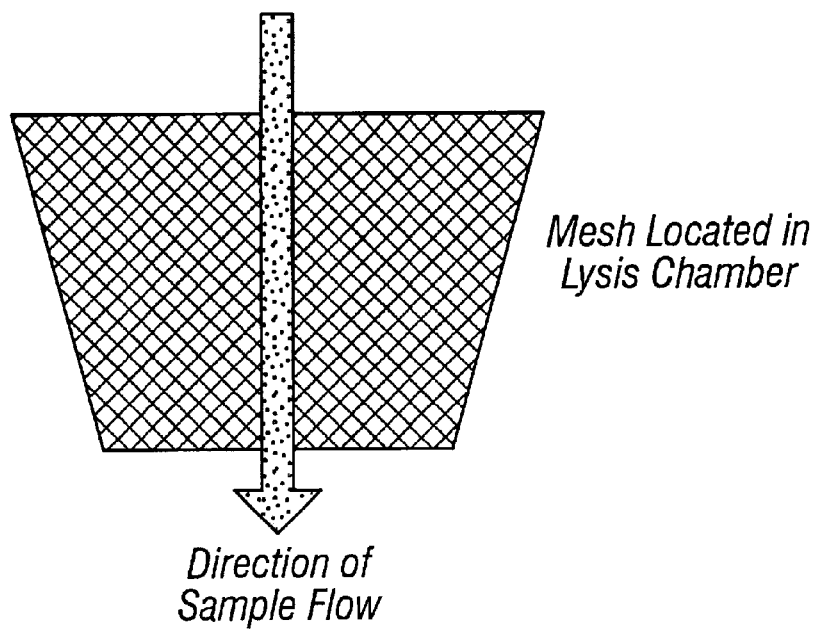
FIG. 1 depicts the orientation of a mesh in a lysis chamber with mesh threads oriented 45 degrees to the direction of sample flow (arrow).

The present invention provides for simple and rapid lysis of cells in biological samples, whereby both the intracellular and extracellular contents of the sample can be analyzed in a single assay.

In accordance with the present invention, a lysis chamber is provided. The lysis chamber contains lytic materials on a surface thereof. The lysis chamber can comprise a mesh in the space delimited by the lysis chamber; in a preferred embodiment the mesh comprises lytic materials(s) thereon.

Preferred lysis chamber embodiments of the invention comprise enclosed chambers of capillary space dimension. Alternatively, a device in accordance with the invention comprises a sample addition region; a fluid access port to the lysis chamber; a lysis chamber; a fluid egress port from the lysis chamber; and, an exit region fluidly connected to the egress port. The device optionally comprises means for producing an assay result in an exit region of the device.

MODES FOR CARRYING OUT INVENTION

This invention provides devices that comprise a lysis chamber that can lead to lysis of cells in biological samples. The lysis chamber is preferably a chamber of capillary space dimension that contains lytic materials on a surface thereof.

The present invention can be used in the context of devices that provide for simple and rapid means of introduction of one or more reagents to a biological sample and/or the removal of undesired components from a biological sample.

Heretofore, devices in the art which are used for the lysis of blood samples, for example, those used for the assay of blood glucose by enzymatic and electrochemical means, incorporated transverse flow of blood through a lysing region. The disadvantages of transverse flow in a lysis region are numerous. For example, the volume of sample that can be lysed is limited by the volume of the lysing region. In addition, hydrostatic pressure is usually necessary to cause the flow of blood or sample transversely through the lysing region. Thus, the current art provides for lysing regions rather than lysing chambers.

Preferred embodiments of devices in accordance with the invention utilize lateral flow of sample through a lysing chamber. The use of capillarity force, and the present teachings concerning the relationship between surface area and volume in the lysing chamber have allowed for lysing chambers which are in fluid communication with downstream capillaries containing certain reagents for performing immunoassays. One skilled in the art will recognize the versatility of the lysing chamber as described herein. The transverse flow of sample through a lysing chamber allows for a great variability in the sample volume while maintaining very efficient lysis of the sample in a small area within the lysing device.

In one embodiment of a lysis chamber in accordance with the invention, a woven mesh is treated with a single reagent, or set of reagents, prior to its being introduced into a lysis chamber which is a capillary space of the device. In such an embodiment, it is preferred that there be a lateral fluid flow path through the mesh, located in a lysis chamber, that is fluidly connected to a sample addition region and to a sample egress port. As fluid moves through the lysis chamber, reagents can be dissolved off of the mesh and introduced into the sample fluid. These reagents can be lytic reagents. Alternatively, specific components can be removed from the sample fluid through various means of capture by reagent(s) bound to the mesh.

The present invention can be utilized in any device format in accordance with the teachings provided herein. In a preferred embodiment, the invention is used with the technology of devices described in U.S. Pat. No. 5,458,852 to Buechler, incorporated herein by reference. Aspects of preferred modes of the invention are discussed below.

Lateral and Transverse Fluid Flow

As used herein, fluid flow will be described as follows: a mesh for use in a chamber in accordance with the invention has width and length dimensions, and substantially smaller depth ("thickness") dimension. For a mesh with such dimensions, transverse flow is perpendicular to the length and width of the mesh, and is predominantly in a direction parallel to the depth of the mesh. Conversely, lateral flow is predominantly parallel to the length or width planes of a mesh. Alternatively, a lateral flow path is a distance greater than a transverse flow path distance through a mesh, typically these flow paths are oriented perpendicular to each other. In one embodiment of the invention, a lateral fluid flow path is through a mesh connecting a fluid access port to a fluid egress port, where the flow path is greater than or equal to that of the greatest cross sectional distance of the mesh as determined perpendicular to any point along the flow path. A preferred embodiment of a device comprising lateral flow is disclosed in U.S. application Ser. No.: 08/704,804, filed Aug. 26, 1996, in the name of Buechler et al.

Lysis Chamber

A lysis chamber in accordance with the invention comprises a surface that contacts sample fluid, when sample is added to a device comprising the chamber; a lytic material is present on this sample-contacting surface. A preferred embodiment of a lysis chamber comprises capillary space dimensions. In a preferred embodiment, the lytic chamber is a capillary space with a lytic material on a lumenal surface thereof.

For example, a lytic material on the surface of a lysis chamber can be saponin or a detergent. Generally, the lysis chamber is in fluid communication with one or more regions in a device. For example, a sample reservoir or sample addition region can be upstream of a lysis chamber, or an exit region can be downstream from a lysis chamber. An exit region can contain a system, such as are known to those of ordinary skill in the art, for achieving an assay result of an analyte to be evaluated in a biological sample. Examples of such systems are immunoassays and assays using enzyme based modifications of analytes.

A preferred embodiment of the lysis chamber comprises a structure to provide additional surface area within the lysis chamber. For example, the structure can be formed of a mesh or matrix. A preferred embodiment of the structure is a mesh. The mesh can contain a lytic reagent or other assay reagent (s) associated therewith.

The ratio of surface area to volume is a parameter of particular interest in designing a lysis chamber. In order to provide rapid sample treatment, it is advantageous to provide a large area for any surface to which reagents are applied. A simple way to achieve a high surface area to volume ratio in a device is to design a chamber with a narrow "gap height" between the floor and ceiling of the chamber. For such an embodiment, the surface area of the chamber, on which reagents can be applied, is essentially the sum of the surface areas of the floor and ceiling. The sample volume is confined in the gap between the floor and ceiling.

An alternative approach to increasing the area of a particular surface is to add texture to surfaces which define the chamber. The addition of dimples or grooves to the ceiling and/or floor increases the surface area of that component.

An alternative and preferred approach to achieving a high surface area (SA) to volume (V) ratio in the lysis chamber is to sandwich a woven material, such as a mesh, between the lid and base. This method of increasing SA/V has a number of distinct advantages relative to those just described.

First, for a fixed sample volume, a particular SA/V can be achieved in a smaller zone, in terms of length and width (not height) by including a mesh. In this embodiment, the total surface area is the sum of that of the ceiling, base and total mesh surface.

A second advantage from use of a mesh is that selected reagents can be applied to the mesh prior to inserting it into the device. The mesh can be treated with reagents in bulk roll form or in long strips. Individual device sized mesh pieces can then be punched out of the treated strip and placed in the device. Without use of a pretreated mesh, the components of the device would be treated individually.

A third advantage to the mesh-based sample pretreatment chamber is its "tunability". Several sizes and types of mesh are commercially available, as reflected by the meshes listed in the first column of Table 1. Aspects such as SA/V, flow rate, sample retention volume, capillarity, treatment homogeneity, and assay performance can be adjusted by selecting a particular mesh, rather than by time-consuming and costly remachining and remolding of the device base, sides and lid.

TABLE 1

| Mesh (Tetko Cat #) | Pore ($\mu$m) | Thickness ($\mu$m) | Sample Vol ($\mu$l) | SA Mesh (mm sq) | Mesh SA/V | Total SA/V | Free Gap (um) |
| --- | --- | --- | --- | --- | --- | --- | --- |
| none | N/A | N/A | 28.0 | N/A | N/A | 7 | 280 |
| 7-210/35 | 210 | 280 | 18.6 | 258 | 14 | 25 | 0 |
| 7-260/41 | 260 | 270 | 19.8 | 226 | 11 | 22 | 10 |
| 7-275/42 | 275 | 265 | 19.7 | 223 | 11 | 22 | 15 |
| 7-285/44 | 285 | 255 | 20.1 | 219 | 11 | 21 | 25 |
| 7-185/36 | 185 | 230 | 20.2 | 253 | 12 | 22 | 50 |
| 7-185/36 | 185 | 230 | 20.2 | 253 | 12 | 22 | 50 |
| 7-290/49 | 290 | 220 | 22.2 | 189 | 8 | 18 | 60 |
| 7-236/44 | 236 | 210 | 21.7 | 211 | 10 | 19 | 70 |
| 7-250/46 | 250 | 203 | 21.9 | 205 | 9 | 19 | 77 |
| 7-265/47 | 265 | 200 | 22.1 | 196 | 9 | 18 | 80 |
| 7-285/55 | 285 | 168 | 23.9 | 163 | 7 | 15 | 112 |
| 7-105/52 | 105 | 61 | 26.3 | 173 | 7 | 14 | 219 |

Lysis Mesh/Matrix

A preferred embodiment of a structure to provide additional surface area in the lysis chamber is a mesh. The mesh can be a fabric material such as nylon, polyester, glass fiber, or polypropylene. As depicted in Table 1, a variety of mesh parameters have been evaluated. These parameters are set forth in the various columns in Table 1: mesh designation, pore size and mesh thickness. In addition, Table 1 shows calculated parameters for the various meshes in a lysis chamber of fixed dimensions 100×100×0.28 mm. The surface area of the mesh relative to the sample volume (capacity) in the chamber (Mesh SA/V), as well as the Total SA/V, which includes the surface area of the mesh and that of the ceiling and base is also presented.

The impact of cutting mesh material at different angles relative to the direction of the weave was evaluated. It was found that when mesh material is cut parallel to the weave, then placed in a lysis chamber of a device, that small streams of nonlysed sample exited the chamber. The nonlysed sample appeared to have moved through the space between the mesh threads. It was found that when mesh is cut at 45 degrees relative to the weave, fluid flow through the capillary was 45 degrees relative to the mesh fibers (FIG. 1); in this embodiment, certain reagents, such as saponin, tended to wash forward. This was evidenced by observing that, after allowing fluid to flow laterally through a mesh, only the downstream region of the mesh contained lysed blood, therefore the lysis agent saponin was only in this region. In this embodiment, no unlysed material exited the chamber. Presumably, this embodiment functioned by sample encountering a torturous path through a capillary space defined by the angle-cut mesh, as there is no straight path through the mesh in the direction of flow. Thus, the effectiveness of the sample treatment by a mesh contained in a capillary space can be modulated by the direction of flow relative to that of the mesh threads.

In addition to providing a surface on which to immobilize lytic materials or assay reagents, surfaces of the mesh can be treated with materials to alter the hydrophobic or hydrophilic character of the mesh. For example, edges of a mesh can be treated with a material such as ink to create regions of increased hydrophobicity. Hydrophobic regions on the mesh can serve to minimize flow in these regions, and are preferably located at the mesh perimeter.

Mesh Material

Several materials are available as woven fabrics. Such as natural meshes, e.g., those made from cotton and silk. Synthetic materials are numerous and include Nylon, glass fibers, polyester and polypropylene, to mention a few. Meshes of blends of natural and synthetics also exist. The selection of material depends on the required performance, nature of the reagents being applied and the nature of the sample fluid. The mesh should be compatible with the reagents and should permit sample fluid to flow through. Issues to be evaluated when selecting a mesh include wetability, chemical resistivity to samples or reagents, stability, uniformity, availability, cost, weave type, thickness, and porosity.

Preferred for the current application is synthetic mesh. Particularly preferred are fabrics made of polyester. Since many treatment solutions are water-based, wettable meshes are typically preferred. It was determined that polyester meshes were more easily wetted than either Nylon or polypropylene. Advantageously, polyester is also chemically resistant to several organic solvents.

Also an issue when selecting a mesh material is the nature of the sample fluid and, perhaps more critical is the nature of the analyte being measured by the device. As the sample will ultimately flow through the mesh contained within the lytic chamber, there is an obvious disadvantage to the device if the analyte under investigation is adsorbed onto the mesh prior to its measurement in e.g., an exit region.

Mesh Filament and Mesh Weave

Meshes are available in both monofilament and multifilament types. While a greater surface area is feasible with a multifilament mesh, the small spaces between the individual filaments that are present, when these filaments are wound to form a thread, are believed to lead to poor reagent dissolution and possibly increased analyte adsorption.

Thus, a presently preferred type of mesh is based on monofilament threads. These threads come in very reproducible diameters, especially in the case of the synthetic materials, and do not have the drawbacks associated with the multifilament type material.

A variety of weave types are also available including square weave, twill weave and Taffeta. The selection of a particular weave can affect such properties of the lysis chamber as flow rate, flow front quality, directional flow, wicking ability and handling ease. While the selection of weave will depend significantly on the device embodiment and sample type, it has been found that the plain square weave was suitable for preferred embodiments of the device.

Mesh Pore Size

Also, relevant to the selection of the appropriate mesh material is the pore size. The size of the pore openings will affect both the flow rate and total surface area, and thus, the overall performance of the lysis chamber. Openings range from a few microns to thousands of microns. In preferred embodiments, mesh pore size is approximately 285 microns.

Mesh Cutting

The mesh can be cut to size by several methods including: simple die cut, shear cut, ultrasonic cutting and heat cutting. The preferred method of cutting is shear cutting. With shear cutting, a strip of treated mesh is fed into a shear cutting punch station where it is punched to a desired shape. The cut meshes are collected for eventual placement into devices. Alternatively, a punch station can be designed to punch and place the cut mesh directly into the device.

Mesh Treatment

Reagent(s) can be applied to the mesh in a number of ways: the mesh can be attached to the base of the device first, and the reagent(s) applied by pipetting directly onto the base/mesh. The combined mesh and base then can be dried prior to device assembly.

A preferred approach to the application of reagents to the mesh is to treat the mesh in bulk form. Mesh can be obtained in 50 yard (or greater) preslit lengths. The mesh strips are threaded through a "reagent application station" where mesh is either dipped into a solution or the solution is applied at a controlled rate by pumps or other application modalities. The strips are then dried, such as by suspending in a drying room. Faster drying is achieved using a convection oven. For example, a convection oven is used that has a rather long drying chamber through which warm dry air is circulated, and which has entrance and exit ports through which a strip of treated mesh is fed. A take-up spool at the exit port of the oven controls the mesh feed rate, such that the mesh is sufficiently dry as it comes out of the oven prior to spooling.

Depending on the nature of the reagents being applied, the application medium can be either aqueous or organic solvent-based.

Mesh Attachment

Mesh can be attached to the device using any of the following approaches: adhesives, ultrasonic welding (in the case of synthetic material) or simple accurate placement in the base followed by permanent attachment of the lid. The preferred method of mesh attachment is to weld the lid to the base, after accurately positioning the mesh in the lysis chamber. This preferred method avoids any complications that might arise due to contamination of the sample or reagents with adhesive materials.

Sample Reservoir

A sample reservoir or sample addition region can be fluidly connected upstream from the lysis chamber. In preferred embodiments, the lysis chamber has equal or greater capillarity than the sample reservoir, to facilitate flow from the sample reservoir to the lysis chamber. Preferably, a sample reservoir accomplishes several functions: 1) it delimits a volume which is sufficient to achieve an assay result, and thus facilitates a device user's ability to provide that volume; 2) it accomplishes the foregoing and allows for a diverse range of input volumes which all allow for an assay result; and, 3) when a reservoir is a capillary space, it helps to prevent fluid from inadvertently escaping the device.

In a preferred embodiment, the sample reservoir contains texture on surfaces thereof. The texture can be in the form of grooves or other protrusions and depressions. As with a lysis chamber, surfaces of the sample reservoir which contact sample fluid can comprise a lytic material or assay reagent associated therewith.

A sample reservoir comprising a capillary space has been incorporated into an assay device, whereby sample was contained in the capillary space of the sample reservoir, and the reservoir was in fluid communication with the lytic chamber. As noted herein, an advantage of utilizing a capillary space for introducing the sample to the device is that the fluid, for example, a hazardous chemical, environmental or biological fluid, contained in a capillary space will tend not to spill or leak from the device.

In a preferred embodiment, lytic materials can be provided on one or more surfaces of a sample reservoir. In such an embodiment, the sample reservoir also functions as a lysis chamber. For clarity herein, however, a sample reservoir, even if it functions as a lysis chamber, is referred to as a sample reservoir. Particular advantages of providing lytic materials in association with a sample reservoir, which is fluidly connected to a lysis chamber, include more complete lysis of a sample added to the device, such that chemical and physical homogeneity can be maintained between the assay and rinse volumes of the sample. For example, if a whole blood sample is not uniformly lysed in different regions of a device, such as a sample reservoir and a lysis chamber, then variations in both the viscosity of the sample, and the availability of the analyte being assayed will yield disparate results. In a preferred embodiment, the volume of fluid retained by the mesh placed in a lysis chamber is the main fraction of the sample to be assayed by the device, once that volume reaches a diagnostic region downstream. Generally, additional sample volume held by the sample reservoir is required for rinsing of the diagnostic lane following assay of the sample fluid. It has been found that rinsing with unlysed blood resulted in higher backgrounds as well as poorly reproducible flow rates. Thus, the addition of one or more lytic materials to the sample reservoir greatly reduced these undesirable phenomena. Furthermore, addition of assay reagents, such as anticoagulants and viscosity modifiers, can be introduced to a rinse volume of the sample via reconstitution from the sample reservoir.

Exit Region in Fluid Communication with the Lysis Chamber

An exit region can be placed in fluid communication with the lysis chamber. Generally, the exit region is downstream from the lysis chamber, and receives sample fluid after material in the sample, such as cells, have been lysed in the lysis chamber. In preferred embodiments, the exit region comprises one, or more, of the components of a system for obtaining an assay result.

Preferably, the exit region comprises equal or higher capillarity relative to the lysis chamber, to facilitate fluid flow therebetween. Also preferred is that the lysis chamber comprise equal or greater capillarity relative to the sample reservoir. Due to the use of capillarity as taught herein, fluid enters then leaves the lysis chamber without an external pressure, and uniformly fills the capillary space of the exit region. Thus, capillary force has been used to cause fluid entrance into the lysis chamber and then egress of fluid from the lysis chamber into the exit region, without the application of an external pressure such as hydrostatic pressure.

Device Assembly

Devices described herein can be assembled by joining several parts. A lysis chamber or other device component(s) can be fabricated from conventional materials compatible with a chemical, environmental or biological fluid to be assayed, for example: a plastic material such as acrylic, polystyrene, polycarbonate, or like polymeric materials; as well as silicon composites, such as silicon semiconductor chips; glass; or metal.

In the case of plastic polymeric materials, device components may be fabricated using thermal injection molding technology or machining. In the case of fabricating from silicon composites, micro machining and photo lithographic techniques, commonly used in the field of electronics, can be utilized to create chambers and capillaries.

Device components such as a lid and base are contacted together in order to form the physical configuration desired to achieve a particular result. Ultrasonic welding, adhesives, physical interfitting and heat welding are some of the methods that may be used to join the base and lid. For example, with embodiments comprising a lid of silicon composite or plastic, and a base of plastic or silicon composite, the base and lid can be joined with adhesives.

In a preferred embodiment, surfaces of base, ceiling, or both are made more hydrophilic or "wettable", whereby the contact angle between the sample fluid meniscus and the base and ceiling is decreased. There are several ways to decrease the contact angle, including but not limited to corona discharge, plasma treatment or the drying down of various surfactants or proteins onto surfaces.

In accordance with standard methodologies, exposing a plastic surface to a corona discharge or plasma gas results in the formation of functional groups on the surface. The surface chemistry as well as the degree of hydrophobicity are thus modified and can be used for a variety of applications. For example, time gates, as described in U.S. Pat. No. 5,458,852 to Buechler (entirely incorporated by reference herein), can be incorporated at the lysis chamber to provide a defined incubation time for the sample within the chamber.

EXAMPLES

One skilled in the art will recognize, in view of the present disclosure, that the lysis chamber can have many design configurations or embodiments. Furthermore, the assay concepts disclosed herein can be incorporated into a variety of devices that can be used in various assays. The following examples demonstrate presently preferred embodiments and are not intended to limit the invention.

Example 1

Performance Tunability of a Lysis Chamber

As mentioned above, one advantage of using a woven material as the substrate for reagents in the lysis chamber is that it allows for tunability. Total surface area, surface area to sample volume ratio, capillarity, sample retention volume, and treatment homogeneity can be adjusted by the proper selection of weave porosity, thread diameter and chamber height. Tables 2, 3, and 4 show the relevant dimensions of several commercially available synthetic meshes. {Tetko Inc., Depew, N.Y.; Ahlstrom Filtration, Mount Holly Springs, Pa.; Pall Corp., Pall BioSupport Division, Glen Cove, N.Y.)

Figure 2:
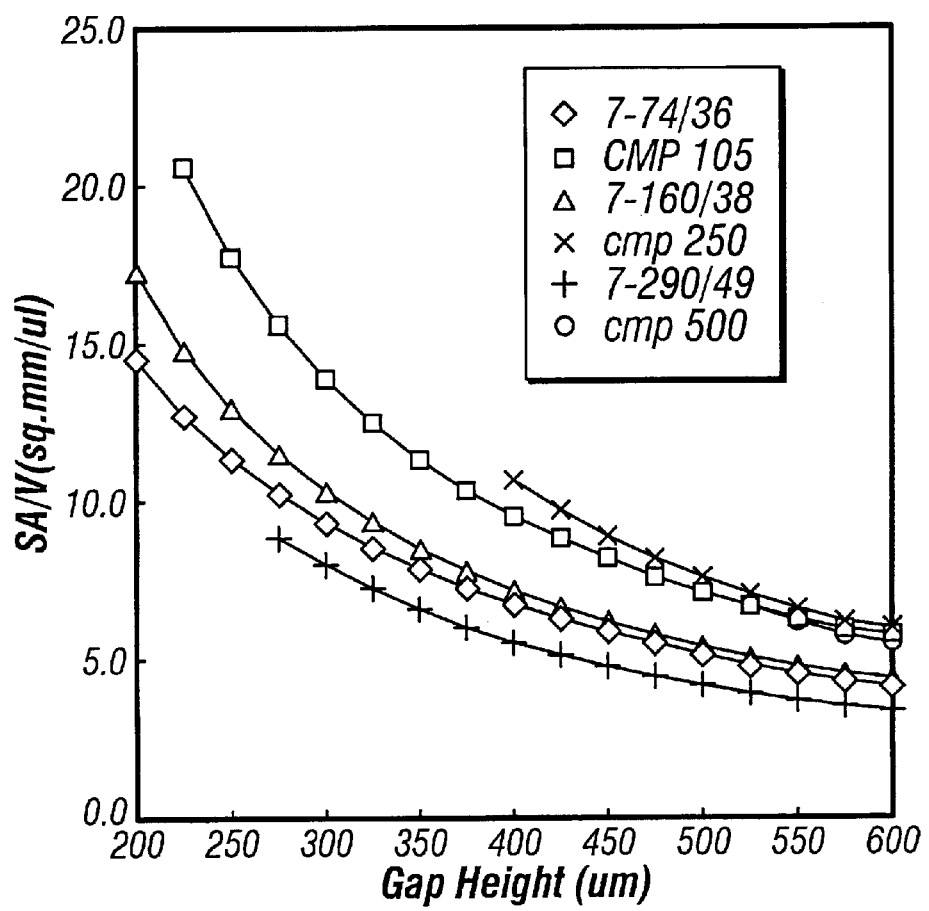
FIG. 2 depicts the ratio of mesh surface area-to-sample volume for several different meshes in lysis chambers of various heights.

FIG. 2 shows the mesh surface area-to-volume ratio of different meshes in lysis chambers of various heights. Note that for a particular gap height, a range of surface area-to-volume values was attained. These values were affected by mesh thickness, mesh porosity and thread thickness.

Although mesh surface area-to-sample volume was important to the performance of the lysis chamber, it is not the only factor in selecting the appropriate material. Also very important are the flow properties of the sample through a lysis chamber containing a mesh, the sample volume retained in the mesh, and the overall effectiveness of any sample pretreatment step.

Additionally, as shown in Table 2, in a chamber of a given height, reducing the pore size of the mesh, while keeping the mesh thickness and gap height fixed, resulted in a lower flow rate, causing an increase in the total assay time. In a fixed gap height (300 μm), increasing the pore size by 20% resulted in a 40% decrease in reaction chamber fill time (Table 2). The thicknesses of the two meshes were essentially identical. Thus, larger pores tended to lead to more rapid fill times.

In Tables 3 and 4 it is seen that in a chamber with a fixed gap height (300 μm), a 25% reduction in mesh thickness (280 to 210 μm) with a 12% increase in pore size (210 to 236 μm) resulted in no change in average lane time. Lane time is defined as the time required to fill, with the lysed sample, a capillary space downstream to the lysing chamber. The lane is also defined as the diagnostic lane as described in U.S. Pat. No. 5,458,852. However, reducing thickness by only 5% (280 to 265 μm) with a 31% increase in pore size (210 to 275 μm) gave a 16% decrease in lane time. Again, larger pores tended to lead to more rapid fill times.

Thus, it was found that the parameter of mesh thickness in a chamber of fixed height, as well as the parameter of pore size affected the relative flow rate of fluid through the mesh.

As appreciated by one of ordinary skill in the art, an increase or decrease in flow rate is an important parameter in determining the total time required to run the assay, and also is relevant to determining the efficiency of sample lysis.

TABLE 2

Affect on Fill Times by Change in Mesh Pore Size

| Mesh (Tetko Cat #) | Thickness (μm) | Pore (μm) | Average Rxn. Chamber Fill Time(s) |
|---|---|---|---|
| 7-210/35 | 280 | 210 | 10 |
| 7-250/35 | 290 | 250 | 6 |

TABLE 3

Affect of Mesh Thickness and Pore Size on Flow Rate

| Mesh (Tetko Cat #) | Thickness (μm) | Pore (μm) | Average Lane Time(s) |
|---|---|---|---|
| 7-210/35 | 280 | 210 | 208 |
| 7-275/42 | 265 | 275 | 175 |
| 7-236/44 | 210 | 236 | 209 |
| None | — | — | 123 |

TABLE 4

| Mesh | Pore (μ) | Thickness (μ) | Gap (μ) | Free Gap (μ) | Rel. Flow Rate | Average Lane Time (Sec.) |
|---|---|---|---|---|---|---|
| (Tetko Cat #) 7-285/44 | 285 | 255 | 280 | 25 | Fast | |
| (Tetko Cat #) 7-275/42 | 275 | 265 | 280 | 15 | Fast | 175 |
| (Tetko Cat #) 7-250/46 | 250 | 203 | 280 | 77 | Medium | |
| (Tetko Cat #) 7-236/44 | 236 | 210 | 280 | 70 | Slow | 209 |
| (Tetko Cat #) 7-210/35 | 210 | 280 | 280 | 0 | Slow | 208 |
| (Tetko Cat #) 7-185/36 | 183 | 230 | 280 | 50 | Slow | |
| Ahlstrom Cytosep #1661 | 2.5 | 210 | 280 | 70 | V. Slow | |
| Pall U2-205 | 2 | 380 (uncompressed) | 280 | 0 | V. Slow | |
| None | — | — | 280 | 280 | Fast | 123 |

Example 2

Blood Lysis

The blood concentration of an analyte of interest is a parameter that can be measured in devices which comprise a lysis chamber in accordance with the invention. There are certain situations where the analyte to be measured is distributed within several of the various blood components. For example, cyclosporin A, an immunosuppressive drug, is found in blood cells, plasma, and bound to lipoproteins. Thus, for an accurate measurement of cyclosporin concentration, an entire whole blood sample must be measured. In order to measure the fraction of drug incorporated within the blood cells, the cells must be lysed. As discussed herein, cell lysis causes the contents of the cell to be accessible to the assay reagents.

In this example, a lysis chamber comprising a mesh was used with lytic materials immobilized thereon. Accordingly, solutions containing various concentrations of a blood lysing agent (saponin) were applied to the mesh for placement in a lysis chamber. The effectiveness of blood lysis was monitored by observing the red-to-brown color change of hemoglobin upon oxidation by the ferricyanide ion. In this example, whole blood was spiked with potassium ferricyanide at a concentration of 6mg/ml. The spiked blood remained red as long as the hemoglobin remained sequestered within the intact red blood cells. Upon cell lysis, the ferricyanide ion had access to the hemoglobin, oxidizing it, and resulting in a brown color. The red-to-brown color change can be observed qualitatively, or measured using a color sensitive camera or other means for colorimetric assessment known to those of ordinary skill in the art.

Figure 3A:
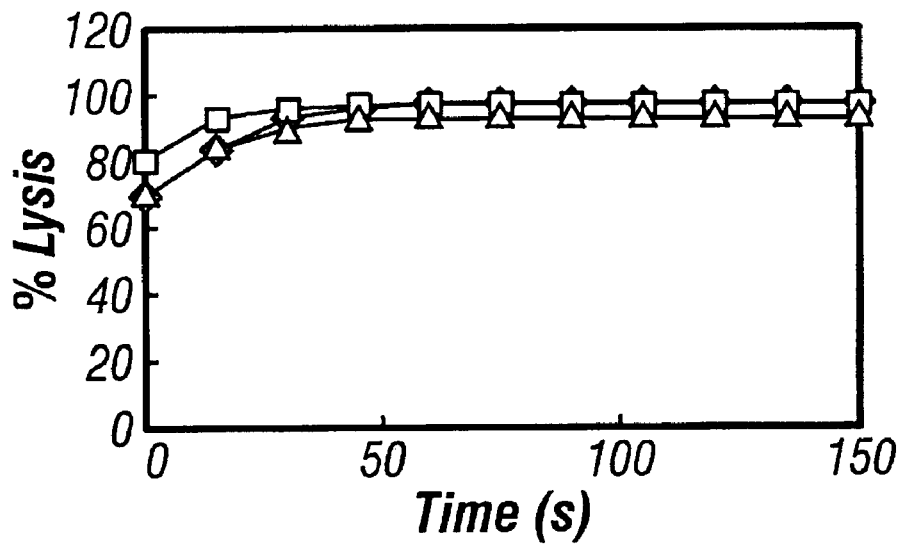
FIG. 3A and FIG. 3B depict the time dependence of red cell lysis measured in a reaction chamber, as a function of lysing agent concentration in the solution applied to the mesh.
Figure 3B:
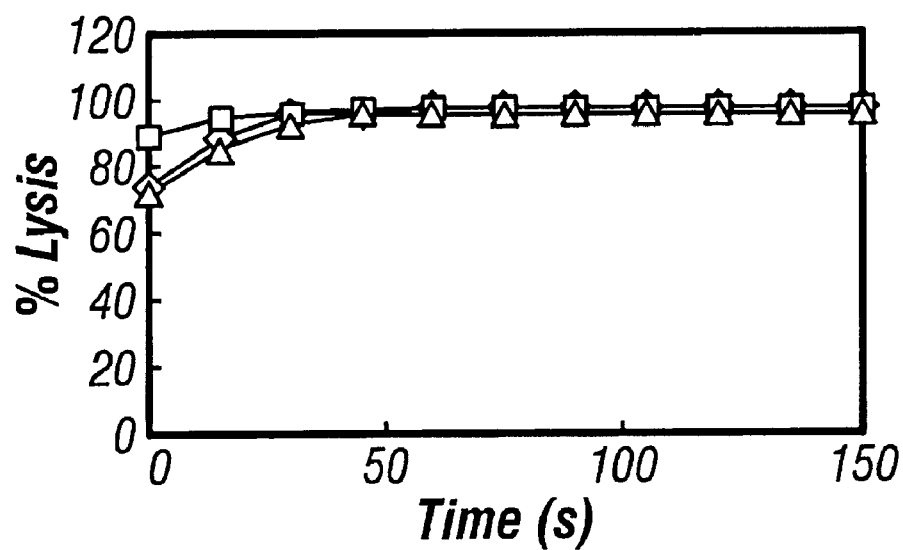

FIG. 3 shows the time dependence of red cell lysis measured in the reaction chamber as a function of lysing agent concentration in the solution applied to the mesh. In this example, the mesh thickness and opening size were 265 $\mu$m and 275 $\mu$m, respectively. The capillary space in which the mesh was located was 280 $\mu$m in height. Each mesh was dipped in aqueous solutions containing 5 or 10 mg/ml saponin followed by air drying. This demonstrates the effectiveness of the lysis chamber of the present invention. Note that increasing the saponin concentration from 5 to 10 mg/ml in the lysis solution applied to the mesh achieved total lysis in a slightly shorter time. Thus, the degree and rate of lysis was modulated by the concentration of the lysing agent with which the mesh is treated. The results show that nearly complete red blood cell lysis was accomplished in less than 50 seconds using several saponin concentrations.

Example 3

Additives

It is often beneficial to add certain reagents to an assay sample to enhance the performance of the assay. A sample addition reservoir and/or a lysis chamber can serve as a zone where such reagents can be introduced into the sample. If a mesh or matrix is located within the lysis chamber, the following materials can be located on the mesh or matrix. Listed below are several examples of materials that can be added:

Anticoagulants—In order to enhance the simplicity of a point of care blood assay, the inclusion of anticoagulants on the device allows the blood sample to be collected by means of a finger stick, rather than collecting venous puncture samples in anticoagulant-containing sample tubes. In preferred embodiments, either EDTA or heparin is applied to surfaces of the sample addition reservoir and lysis chamber, and/or mesh or matrix within the lysis chamber. Thus, as the sample passes through the sample reservoir or lysis chamber, the anticoagulant is reconstituted and affects its action on the sample.

Sample Viscosity Modifiers—The performance of subject devices depend greatly on the flow rate of the sample through the device. Although the sample flow rate can be affected by such variables as gap height, mesh pore size, and surface wetability, it is sometimes advantageous to modify the viscosity of the sample in addition to, or rather than, the design of one or more device components.

For example, the flow rate of lysed blood in the device was reduced significantly by the addition of either tetraalkylammonium salts or alkylureas to the lysis chamber or sample reservoir. Alternatively, the viscosity of a sample can be increased by the addition of protein and/or polymers to result in slower flow. In a preferred embodiment, these reagents are added to the sample addition reservoir, the lysis chamber and/or the mesh as a solution which was then dried. The viscosity modifiers were then reconstituted in the sample addition reservoir, lysis chamber and/or mesh upon addition of fluid.

Nonspecific Binding (NSB) Inhibitors—Nonspecific binding of certain assay reagents to each other and to device components is often a problem in diagnostic assays. This is particularly a problem when an antibody recognizes a region of a molecule that is not its antigen. This can lead to high background reactions and false positive (or negative) assay results. NSB inhibitors include those discussed in application Ser. No.: 08/101,677, now issued as U.S. Pat. No. 5,525,524. The addition of NSB inhibitors to the sample often relieves this problem. Such NSB inhibitors are added to the mesh solution, such that as the sample passes through the mesh, the NSB inhibitors are introduced to the sample. A further example is the introduction of an immunoglobulin inhibiting reagent (e.g., IIR®, Bioreclamation Inc., East Meadow, N.Y.) to the sample via methodologies known to those of ordinary skill in view of the present disclosure, to prevent reaction of human antibodies with the antibodies utilized in the immunoassay. For example, the immunoglobulin inhibiting reagent can be added to the lysis chamber, the sample reservoir, or to the sample prior to the assay. Also, bovine IgG can be used to prevent nonspecific binding to receptors used in an assay device in accordance with the invention; the bovine IgG also can be added by methodologies known to those in the art.

Salts, Buffers, etc.—If needed for a particular assay embodiment, the sample addition reservoir and/or lysis chamber are areas where salts and/or buffers can be added to the sample fluid. For example, these materials can be applied to a sample reservoir or lysis chamber as liquid which is subsequently dried on the mesh, or as an already dry material.

Furthermore, a wetting agent such as Elvanol (DuPont) or methanol can be used to facilitate wetting of the mesh during the process of applying the agents thereto. As a buffer, BES, can preferably be used to buffer the fluid being applied to the mesh to approximately pH 6.5; saponin in water has a pH of approximately 5.0. A pH of approximately 5.0 might denature proteins or not be optimal for antibody binding or enzymatic activity in an assay fluid; by buffering to a pH of approximately 6.5, these factors can be avoided.

Displacing Reagents—Additionally, a displacing agent can be used to displace an analyte of interest from a carrying molecule. For example, cyclosporin is bound to cyclophilin in blood. In conventional assays, cyclosporin must first be liberated from cyclophilin by extracting blood with methanol prior to its assay. This is not a convenient procedure for a point of care system. An alternative approach is to utilize a displacer molecule, which acts as an analog to cyclosporin and affects the displacement of cyclosporin from cyclophilin. Thus, the displacer molecule can be introduced to the sample via the sample reservoir and/or lysis chamber. (See, e.g. P.C.T. International Publication Number: WO 95/07468, published Mar. 16, 1995). For example, a displacing molecule that has similar affinity for cyclophilin, but which is present at a higher concentration than cyclosporin, will compete with cyclosporin for binding to cyclophilin. Due to the higher concentration of the displacing agent, it will essentially become bound to all cyclophilin, thereby displacing the cyclosporin into solution. When cyclosporin is so displaced, it becomes available to be analyzed.

Alternatively, an analyte can be bound to a carrying molecule, where the analyte alone is not soluble in the assay fluid but the addition of, for example, a surfactant, various solubilizing polymers, or peptides can be used to displace or solubilize an analyte in a sample.

Example 4

Component Removal

There are cases where the removal of an interfering substance (e.g. a ligand) from a fluid sample will be required for proper analyte assay performance. Alternatively, in some cases, simply reducing the sample concentration of a sample component (e.g. a ligand) will enhance the performance of the assay. For such embodiments, a ligand receptor is immobilized onto the sample addition reservoir, lysis chamber and/or the mesh. Thus, as the sample flows through the sample addition reservoir and/or lysis chamber, the ligand of interest binds to the receptor and is either entirely removed from the sample, or its concentration reduced. Such receptors include antibodies, or natural or synthetic components thereof, ion chelators, nucleic acids, and other protein receptors.

In alternative embodiments, a ligand is immobilized on the mesh surface to achieve removal of a corresponding receptor from the sample, where removal or reduction of receptor from the sample is desired.

Figure 4:
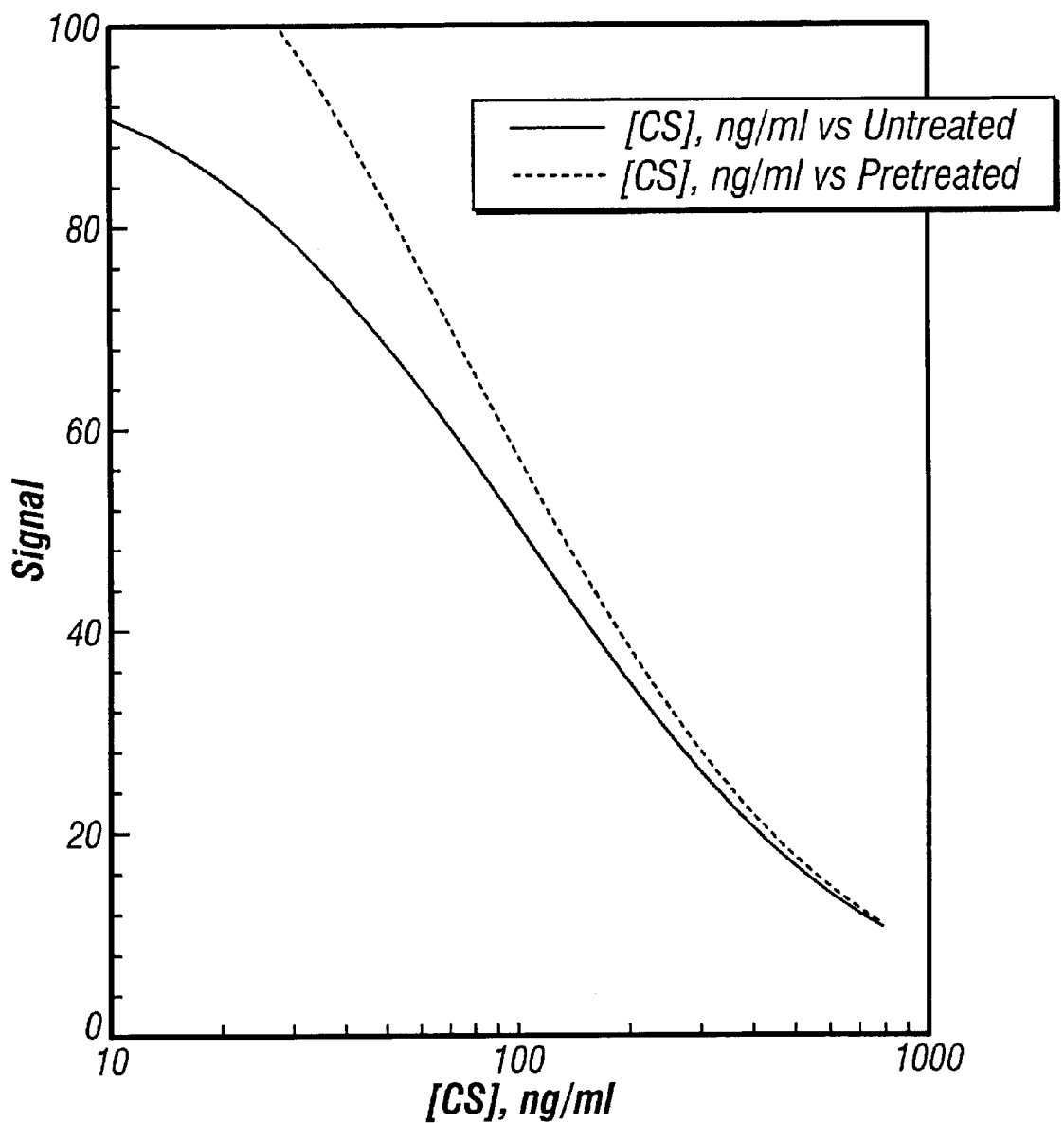
FIG. 4 depicts the dose response behavior of a competitive cyclosporin (CS) assay. The effect of removing 25 ng/ml CS from a blood sample was calculated and depicted in the figure by use of a device comprising a preferred embodiment of a lysis chamber.

In one example, the reduction of blood cyclosporin (CS) concentration by 25 ng/ml yields a more sensitive assay response over a specific dose range. This was accomplished by addition of a cyclosporin antibody to the lysis chamber at a concentration which bound an equivalent of 25 ng/ml cyclosporin (CS). FIG. 4 shows the calculated response of a cyclosporin assay before (untreated) and after (pretreated) the removal of 25 ng/ml CS. While an initial response delay is noted in the "pretreated" sample, the post-delay assay slope is steeper than that of the untreated sample.

Example 5

Hemoglobin A1c Assay

A device comprising a lysis chamber in accordance with the present invention is utilized to assay for hemoglobin A1c (HbA1c). It is known that HbA1c must be evaluated in both extra-cellular and intra-cellular spaces in blood to obtain an effective assay result. Accordingly, a blood sample is added to a device comprising a lysis chamber in accordance with the present invention. Preferably, saponin is used as a lytic reagent. It is also preferable that a sample addition region fluidly connected upstream of the lysis chamber also contain lytic reagents therein. The use of a sample addition region comprising lytic reagents in addition to a lysis chamber in accordance with the invention facilitates a more complete lysis of sample materials, such as blood. Downstream of the lysis chamber is an assay region wherein capture receptors (such as polyclonal antibodies, monoclonal antibodies, recombinantly produced proteins capable of specific binding, or a fragment of any of the foregoing) capable of specifically binding to HbA1c, bind any HbA1c in the sample. Thereafter, conjugated receptors, such as polyclonal or monoclonal antibodies, that are capable of producing a signal, and which also bind to HbA1c when it is bound to capture receptors are presented to the assay region. HbA1c molecules bound to the assay region, e.g., by monoclonal antibodies specific for the analyte now become bound by conjugated analyte-specific antibodies. Accordingly, the signal generated by the conjugated antibody identifies the presence or amount or HbA1c in the sample.

Closing

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention pertains. Although any methods and materials similar to equivalent to those described herein can be used in the practice or testing of the invention, the preferred methods and materials are now described. All publications mentioned herein are incorporated fully by reference herein.

What is claimed is:

1. An assay device comprising:
a lysis chamber comprising a capillary space formed by at least two surfaces spaced a capillary distance apart,
a mesh or matrix within said capillary space, and
a lytic material immobilized on said mesh or matrix, wherein when a sample fluid is added to said assay device, cells contained within said sample fluid contact said mesh or matrix and are lysed by said lytic material.

2. The assay device of claim 1 wherein the lytic material is saponin or a detergent.

3. The assay device of claim 1, wherein the sample fluid is a whole blood sample, and whereby red blood cells are lysed.

4. The assay device of claim 1, wherein said lysis chamber further comprises one or more reagents selected from the group consisting of an agent for displacing an analyte from a carrier molecule, an anticoagulant, a viscosity modifier, a nonspecific binding inhibitor, a salt a buffer, and a wetting agent.

5. The assay device of claim 4, wherein the agent for displacing an analyte comprises an extraction agent, or comprises a molecule that has binding affinity for the carrying molecule for the analyte of interest.

6. The assay device of claim 1, wherein the mesh or matrix further comprises one or more reagents immobilized thereon selected from the group consisting of an anticoagulant, a viscosity modifier, a nonspecific binding inhibitor, a salt, a buffer, a wetting agent, and, an agent for displacing an analyte of interest from a carrying molecule for the analyte of interest.

7. The assay device of claim 6 wherein the agent for displacing an analyte comprises an extraction agent, or comprises a molecule that has binding affinity for the carrying molecule for the analyte of interest.

8. The assay device of claim 1, wherein the mesh comprises a first plurality of fibers oriented substantially parallel to one another, and a second plurality of fibers oriented substantially parallel to one another and oriented substantially perpendicular to the first array of fibers;

wherein there is a direction of fluid flow through the assay device; and, wherein the direction of fluid flow is substantially orientated at a 45 degree angle relative to the first plurality of fibers and relative to the second plurality of fibers.

9. An assay device comprising in fluid connection:

a sample addition region to receive a sample fluid;

a lysis chamber in fluid communication with said sample addition region, said lysis chamber comprising a mesh or matrix comprising a lytic material immobilized thereon, wherein cells contained within said sample fluid contact said mesh or matrix and are lysed by said lytic material; and, an analysis region in fluid communication with said lysis chamber adapted to immobilize for detection an analyte of interest present in intracellular and/or extracellular components of said sample fluid.

10. The assay device of claim 9, wherein the sample addition region further comprises on a surface thereof one or more reagents selected from the group consisting of a lytic material, an anticoagulant, a viscosity modifier, a nonspecific binding inhibitor, a salt, a buffer, a wetting agent, and an agent for displacing an analyte from a carrier molecule.

11. The assay device of claim 9 wherein the sample addition region delimits a capillary space.

12. The assay device of claim 11 wherein a mesh or matrix is located within the capillary space.

13. The assay device of claim 12 wherein the mesh or matrix further comprises one or more reagents immobilized thereon selected from the group consisting of a lytic material, an anticoagulant, a viscosity modifier, a nonspecific binding inhibitor, a salt, a buffer, a wetting agent, and an agent for displacing an analyte from a carrier molecule.

14. The assay device of claim 9, further comprising a second lysis chamber, said second lysis chamber downstream from the sample addition region and the first lysis chamber and upstream of said analysis region, said lysis chamber comprising a mesh or matrix comprising a lytic material immobilized thereon, wherein cells contained within said sample fluid contact said mesh or matrix and are lysed by said lytic material.

* * * * *